US00PP18620P2

(12) United States Plant Patent
Klemm

(10) Patent No.: US PP18,620 P2
(45) Date of Patent: Mar. 18, 2008

(54) ***GERANIUM* PLANT NAMED 'KLEPP05113'**

(50) Latin Name: *Pelargonium peltatum*
Varietal Denomination: KLEPP05113

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/527,833

(22) Filed: Sep. 27, 2006

(51) Int. Cl.
*A01H 5/00* (2006.01)

(52) U.S. Cl. ..... Plt./332
(58) Field of Classification Search ..... Plt./332
See application file for complete search history.

(56) References Cited

U.S. PATENT DOCUMENTS

PP15,311 P2 * 11/2004 Klemm ..... Plt./332

OTHER PUBLICATIONS

UPOV ROM GTITM Computer Database, GTI Jouve Retrieval Software 2007/02 Citation for 'KLEPP05113'.*

* cited by examiner

*Primary Examiner*—Wendy Haas
(74) *Attorney, Agent, or Firm*—C. A. Whealy

(57) ABSTRACT

A new and distinct cultivar of Ivy *Geranium* plant named 'KLEPP05113', characterized by its outwardly spreading to trailing plant habit; freely branching habit; freely flowering habit; double red purple-colored flowers; and good garden performance.

1 Drawing Sheet

Botanical designation: *Pelargonium peltatum.*
Cultivar denomination: 'KLEPP05113'.

BACKGROUND OF THE INVENTION

The present invention relates to a new and distinct cultivar of Ivy *Geranium*, botanically known as *Pelargonium peltatum,* and hereinafter referred to by the name 'KLEPP05113'.

The new Ivy *Geranium* is a product of a planned breeding program conducted by the Inventor in Stuttgart, Germany. The objective of the breeding program is to create new freely-branching and uniform Ivy *Geranium* cultivars with early flowering habit and attractive foliage and flower coloration.

The new Ivy *Geranium* originated from a cross-pollination made by the Inventor in Stuttgart, Germany in 2000 of a proprietary selection of *Pelargonium peltatum* identified as code number PM 140, not patented, as the female, or seed, parent with a proprietary selection of *Pelargonium peltatum* identified as code number PM 115, not patented, as the male, or pollen, parent. The cultivar KLEPP05113 was discovered and selected by the Inventors as a single flowering plant from within the progeny of the stated cross-pollination in a controlled environment in Stuttgart, Germany in 2001.

Asexual reproduction of the new Ivy *Geranium* by vegetative terminal cuttings in a controlled environment in Stuttgart, Germany since 2001, has shown that the unique features of this new Ivy *Geranium* are stable and reproduced true to type in successive generations.

SUMMARY OF THE INVENTION

The cultivar KLEPP05113 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'KLEPP05113'. These characteristics in combination distinguish 'KLEPP05113' as a new and distinct cultivar of Ivy *Geranium*:

1. Outwardly spreading to trailing plant habit.
2. Freely branching habit.
3. Freely flowering habit.
4. Double red purple-colored flowers.
5. Good garden performance.

Plants of the new Ivy *Geranium* differ primarily from plants of the female parent selection in the following characteristics:

1. Plants of the new *Geranium* are more compact than plants of the female parent selection.
2. Plants of the new *Geranium* flower later than plants of the female parent selection.
3. Plants of the new *Geranium* and the female parent selection differ in flower color as plants of the female parent selection have violet-colored flowers.

Plants of the new Ivy *Geranium* differ primarily from plants of the male parent selection in the following characteristics:

1. Plants of the new *Geranium* are less compact than plants of the male parent selection.
2. Plants of the new *Geranium* and the male parent selection differ in flower color as plants of the male parent selection have salmon pink-colored flowers.

Plants of the new Ivy *Geranium* can be compared to plants to the *Pelargonium peltatum* cultivar KLEP02038, disclosed in U.S. Plant Pat. No. 15,311. In side-by-side comparisons conducted in Stuttgart, Germany, plants of the new Ivy

*Geranium* differed from plants of the cultivar KLEP02038 in the following characteristics:

1. Plants of the new Ivy *Geranium* were more compact than plants of the cultivar KLEP02038.
2. Plants of the new Ivy *Geranium* had larger flower petals than plants of the cultivar KLEP02038.
3. Plants of the new Ivy *Geranium* and the cultivar KLEP02038 differed in flower color as plants of the cultivar KLEP02038 had dark red-colored flowers.

BRIEF DESCRIPTION OF THE PHOTOGRAPH

The accompanying colored photograph illustrates the overall appearance of the new Ivy *Geranium*, showing the colors as true as it is reasonably possible to obtain in colored reproductions of this type. Colors in the photograph may differ slightly from the color values cited in the detailed botanical description which accurately describe the colors of the new Ivy *Geranium*. The photograph comprises a close-up view of a typical inflorescence and leaves of 'KLEPP05113'.

DETAILED BOTANICAL DESCRIPTION

The photographs and following observations, measurements and values describe plants grown in Stuttgart, Germany in 12-cm containers in a glass-covered greenhouse during the summer and autumn and under conditions which closely approximate commercial *Geranium* production. During the production of the plants, day temperatures ranged from 18° C. to 22° C., night temperatures ranged from 14° C. to 18° C. and light levels ranged from 20,000 lux to 55,000 lux. Plants were about 2.5 months old when the photograph and the description were taken. In the detailed description, color references are made to The Royal Horticultural Society Colour Chart, 2001 Edition, except where general terms of ordinary dictionary significance are used.

Botanical classification: *Pelargonium peltatum* cultivar KLEPP05113.

Parentage:

*Female, or seed, parent.*—Proprietary selection of *Pelargonium peltatum* identified as code number PM 140, not patented.

*Male or pollen parent.*—Proprietary selection of *Pelargonium peltatum* identified as code number PM 115, not patented.

Propagation:

*Type.*—By vegetative terminal cuttings.

*Time to initiate roots, summer.*—About eight days at temperatures of 22° C.

*Time to initiate roots, winter.*—About nine days at temperatures of 20° C.

*Time to produce a rooted young plant, summer.*—About 18 days at temperatures of 22° C.

*Time to produce a rooted young plant, winter.*—About 21 days at temperatures of 20° C.

*Root description.*—Medium in thickness, fibrous; white in color.

*Rooting habit.*—Freely branching, moderate dense.

Plant description:

*Plant/growth habit.*—Outwardly spreading to trailing plant habit, mounding; densely foliaged. Moderately vigorous growth habit. Freely basal branching habit with about six to seven lateral branches per plant.

*Plant height, to top of umbels.*—About 28 cm to 35 cm.

*Plant height, to top of leaves.*—About 25 cm to 30 cm.

*Plant width.*—About 25 cm to 30 cm.

*Lateral branches.*—Length: About 8 cm to 10 cm. Internode length: About 0.8 cm to 1.4 cm. Texture: Smooth, glabrous. Color: 137C.

Foliage description:

*Arrangement.*—Alternate; simple.

*Length.*—About 6 cm to 7 cm.

*Width.*—About 7 to 8 cm.

*Shape.*—Ivy-shaped.

*Apex.*—Acute.

*Base.*—Cordate.

*Margin.*—Entire.

*Venation pattern.*—Palmate.

*Texture, upper surface.*—Slightly pubescent.

*Texture, lower surface.*—Smooth, glabrous.

*Color.*—Developing foliage, upper and lower surfaces: 138A. Fully developed, upper surface: 146A; venation, 147C. Fully developed, lower surface: 147B; venation, 147C. Zonation pattern: Not observed. Petiole: Length: About 5 cm to 7 cm. Diameter: About 2 mm. Texture, upper and lower surfaces: Rough. Color, upper and lower surfaces: 147C.

Flower description:

*Flower arrangement.*—Double rotate flowers arranged in rounded hemispherical umbels arising from apical leaf axils. Umbels displayed above the foliage on strong peduncles. Flowers face upright to outward; flowers slightly cupped. Flowers not persistent. Flowers not fragrant.

*Quantity of flowers.*—Freely flowering habit; about 10 to 15 flower buds and open flowers per umbel.

*Flowering season.*—Year-round under greenhouse conditions. In the garden in Stuttgart, Germany, flowering is continuous from spring until frost in autumn.

*Flower longevity.*—Individual flowers last about eight days on the plant.

*Umbel height.*—About 5 cm to 6 cm.

*Umbel diameter.*—About 5 cm to 6 cm.

*Flower diameter.*—About 4.5 cm to 5 cm.

*Flower depth (height).*—About 1.5 cm.

*Flower buds.*—Length: About 6 mm to 10 mm. Diameter: About 3 mm to 7 mm. Shape: Elliptic. Color: 138B.

*Petals.*—Quantity per flower: About 10 to 14. Length: About 2 cm. Width: About 1.4 cm. Shape: Ovate. Apex: Rounded. Base: Attenuate. Margin: Entire. Texture, upper and lower surfaces: Smooth, glabrous; velvety. Color: When opening, upper surface: 60A. When opening, lower surface: 64D. Fully opened, upper surface: 60B; venation, 60A; color becoming closer to 64A with development. Fully opened, lower surface: 64D; venation, 60B.

*Petaloids.*—Quantity per flower: None to about six. Length: About 2 mm to 10 mm. Width: About 2 mm to 5 mm. Shape: Irregularly shaped. Apex: Rounded. Base: Attenuate. Margin: Entire. Texture, upper and lower surfaces: Smooth, glabrous; velvety. Color: When opening, upper surface: 60A. When opening, lower surface: 64D. Fully opened, upper surface: 60B; venation, 60A; color becoming closer to 64A with development. Fully opened, lower surface: 64D; venation, 60B.

*Sepals.*—Quantity per flower: Five, arranged in a single whorl. Length: About 0.8 cm to 1.2 cm. Width:

About 4 mm to 6 mm. Shape: Elliptic. Apex: Acute. Base: Obtuse. Margin: Entire. Texture, upper and lower surfaces: Pubescent; rough. Color, upper and lower surfaces: 137C.

*Peduncle* (*umbel stem*).—Length: About 8 cm to 12 cm. Diameter: About 3 mm to 5 mm. Strength: Moderately strong. Angle: Mostly erect. Texture: Slightly pubescent. Color: 138C.

*Pedicel* (*individual flower stem*).—Length: About 1.5 cm to 2 cm. Diameter: About 1.5 mm. Strength: Moderately strong. Angle: Erect to about 110° C. from vertical. Texture: Slightly pubescent. Color: 138C.

*Reproductive organs.*—Androecium: Stamen quantity per flower: About five. Anther length: About 4 mm. Anther shape: Ovate. Anther color: 60C. Pollen amount: Moderate. Pollen color: 32A. Gynoecium: Pistil quantity per flower: One. Pistil length: About 8 mm. Stigma shape: Tapering; reflexed. Stigma color: 60C. Style length: About 3 mm. Style color: 60C. Ovary color: 137D.

*Seed.*—Seed development has not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind and temperatures ranging from about 6° C. to about 33° C. and have demonstrated good garden performance.

It is claimed:

1. A new and distinct Ivy *Geranium* plant named 'KLEPP05113' as illustrated and described.

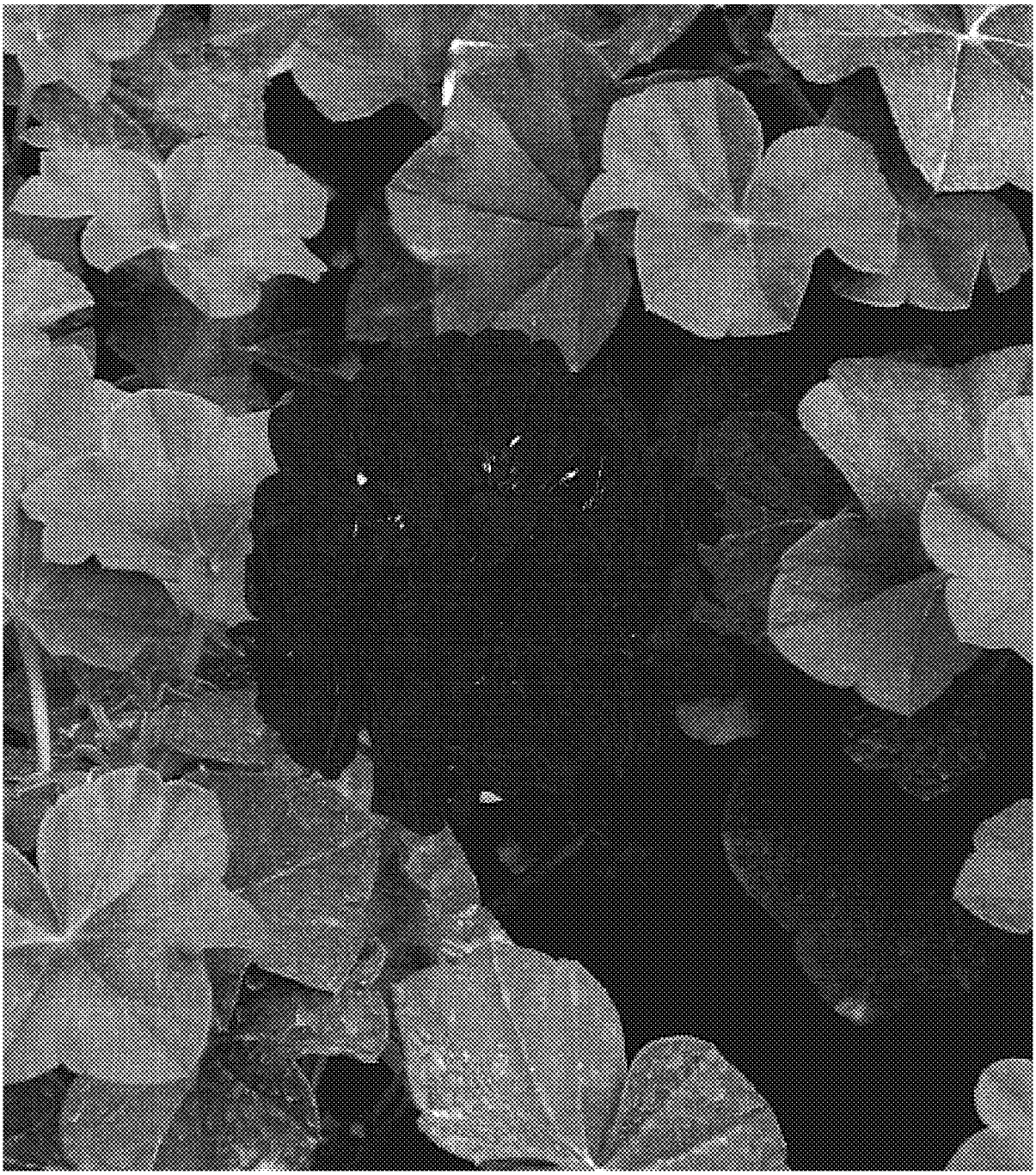

* * * * *